(12) United States Patent
Rodriguez Cutillas

(10) Patent No.: US 9,879,304 B2
(45) Date of Patent: Jan. 30, 2018

(54) METHODS FOR QUANTIFYING ACTIVITY OF PROTEIN MODIFYING ENZYMES

(71) Applicant: Queen Mary & Westfield College, University of London, London (GB)

(72) Inventor: Pedro Rodriguez Cutillas, London (GB)

(73) Assignee: Queen Mary & Westfield College, University of London, London (GB)

( * ) Notice: Subject to any disclaimer, the term of this patent is extended or adjusted under 35 U.S.C. 154(b) by 0 days.

(21) Appl. No.: 14/384,151

(22) PCT Filed: Mar. 8, 2013

(86) PCT No.: PCT/EP2013/054764
§ 371 (c)(1),
(2) Date: Sep. 9, 2014

(87) PCT Pub. No.: WO2013/132075
PCT Pub. Date: Sep. 12, 2013

(65) Prior Publication Data
US 2015/0044713 A1    Feb. 12, 2015

(30) Foreign Application Priority Data

Mar. 9, 2012   (GB) .................................. 1204278.4

(51) Int. Cl.
*C12Q 1/48*   (2006.01)
(52) U.S. Cl.
CPC ......... *C12Q 1/485* (2013.01); *G01N 2560/00* (2013.01)
(58) Field of Classification Search
CPC ........................... C12Q 1/485; G01N 2560/00
USPC .......................................................... 435/15
See application file for complete search history.

(56) References Cited

U.S. PATENT DOCUMENTS

| | | | |
|---|---|---|---|
| 6,818,484 B2 | 11/2004 | Voutsas | |
| 2003/0153007 A1 | 8/2003 | Chen et al. | |
| 2005/0164324 A1 | 7/2005 | Gygi | |
| 2006/0148093 A1 | 7/2006 | Gygi et al. | |
| 2008/0221802 A1 | 9/2008 | Oda et al. | |

FOREIGN PATENT DOCUMENTS

| | | | |
|---|---|---|---|
| WO | 2003/097867 A1 | 11/2003 | |
| WO | 2003/102220 A2 | 12/2003 | |
| WO | 2005/106923 A2 | 11/2005 | |
| WO | 2007/127767 A2 | 11/2007 | |
| WO | 2007/144606 A2 | 12/2007 | |
| WO | 2010/006333 A2 | 1/2010 | |
| WO | 2010/040024 A2 | 4/2010 | |
| WO | 2010/119261 A1 | 10/2010 | |
| WO | WO2011109440 | 9/2011 | |

OTHER PUBLICATIONS

Glinski et al. Stable Isotope Labeling of Phosphopeptides for Multiparallel Kinase Target Analysis and Identification of Phosphorylation Sites; Rapid Communications in Mass Spectrmetry, vol. 17 (2003) pp. 1579-1584.*

Benjamini et al. Controlling the False Discovery Rate: A Practical and Powerful Approach to Multiple Testing; Journal of the Royal Statistical Society B, vol. 57, No. 1 (1995) pp. 289-300.*

Huang et al. Application of Pearson Correlation Coefficient (PCC) and Kolmogorov-Smirnov Distance (KSD) Metrics to Identify Disease Specific Biomarker Genes; BMC Bioinformatics, vol. 11, Suppl 4, (2010) pp. 1-2.*

Alcolea et al. "In-Depth Analysis of Protein Phosphorylation by Multidimensionallon Exchange Chromatography and Mass Spectrometry." Meth. Mol. Biol. 658(2010):111-126.

Alcolea et al., "Increased Confidence in Large-Scale Phosphoproteomics Data by Complementary Mass Spectrometric Techniques and Matching of Phosphopeptide Data Sets", J Proteome Res. 2009 (8)8:3808-3815.

Alessi et al. "Molecular Basis for the Substrate Specificity of Protein Kinase B; Comparison with MAPKAP Kinase-1 and p70 S6 Kinase." FEBS Lett. 399(1996):333-338.

(Continued)

*Primary Examiner* — Scott Long
*Assistant Examiner* — Paul Martin
(74) *Attorney, Agent, or Firm* — Stradley Ronon Stevens & Young, LLP

(57) ABSTRACT

The present invention provides a method of quantifying the activity of a protein modifying enzyme in a sample, comprising: (i) grouping modified peptides from a first sample and modified peptides from a second sample into a single group according to one of the following parameters: (a) modified peptides having a modification site that is modified by the same protein modifying enzyme; or (b) modified peptides having a modification site that is part of the same modification motif; (ii) calculating enrichment of the modified peptides from the first sample compared to the modified peptides from the second sample in the group; and (iii) calculating the statistical significance of said enrichment; wherein a statistically significant enrichment is indicative of a protein modifying enzyme being activated in the first sample compared to the second sample. In some embodiments, the method further comprises identifying modified peptides in a first sample and a second sample using mass spectrometry (MS) prior to step (i).

15 Claims, 8 Drawing Sheets

(56) References Cited

OTHER PUBLICATIONS

Bantscheff et al. "Quantitative Chemical Proteomics Reveals Mechanisms of Action of Clinical ABL Kinase Inhibitors." Nat. Biotechnol. 25.9(2007):1035-1044.
Barglow et al., Activity-based protein profiling for the functional annotation of enzymes, Nat Methods. 2007 4 (10):822-7.
Blagoev et al. "Temporal Analysis of Phosphotyrosine-dependent Signaling Networks by Quantitative Proteomics." Nat. Biotech 22.9(2004):1139-1145.
Blethrow, et al., Covalent capture of kinase-specific phosphopeptides reveals Cdk1-cyclin B substrates, PNAS 2008 105(5):1442-7.
Bodenmiller et al. "Phosphoproteomic Analysis Reveals Interconnected System-Wide Responses to Perturbations of Kinases and Phosphatases in Yeast." Sci. Signal. 3.153(2010):rS4.
Cartlidge et al. "The tRNA Methylase METTL 1 is Phosphorylated and Inactivated by PKB and RSK in vitro and in Cells." EMBO J. 24.9(2005):1696-1705.
Casado et al., A self-validating quantitative mass spectrometry method for assessing the accuracy of high-content phosphoproteomic experiments, Molecular & Cellular Proteomics 2011 10:M110 003079.
Cutillas et al., Biological signalling activity measurements using mass spectrometry, J Biochem 2011 434:189-199.
Cutillas et al., Quantification of gel-separated proteins and their phosphorylation sites by LC-MS using unlabeled internal standards: analysis of phosphoprotein dynamics in a B cell lymphoma cell line, Mol Cell Proteomics. 2005 4 (8):1038-51.
Cutillas et al., Quantitative profile of five murine core proteomes using label-free functional proteomics, Molecular & Cellular Proteomics 2007 6(9):1560-1573.
Cutillas et al., Ultrasensitive and absolute quantification of the phosphoinositide 3-kinase/Akt signal transduction pathway by mass spectrometry, Proc Natl Acad Sci 2006 103(24):8959-8964.
Dayon et al., Relative quanitification of proteins in human cerebrospinal fluids by MS/MS using 6-plex isobaric tags, Anal Chem 2008 80(8):2921-2931.
Dinkel et al., Phospho.ELM: a database of phosphorylation sites—update 2011, Nucleic Acids Research 2011 39: D261-D267.
Ficarro et al., Automated immobilized metal affinity chromatography/nano-liquid chromatography/electrospray ionization mass spectrometry platform for profiling protein phosphorylation sites, Rapid Commun Mass Spectrom. 2005 19(1):57-71.
Frewen et al., Analysis of peptide MS/MS spectra from large-scale proteomics experiments using spectrum libraries, Anal Chem 2006 78:5678-5684.
Gerber et al., Absolute quantification of proteins and phosphoproteins from celllysates by tandem MS, PNAS 2003 100 (12):6940-5.
Gygi et al., Quantitative analysis of complex protein mixtures using isotope-coded affinity tags, Nature Biotechnology 1999 17:994-999.
Hornbeck et al., PhosphoSite: a bioinformatics resource dedicated to physiological protein phosphorylation, Proteomics 2004 4:1551-1561.
Huang et al., Bioinformatics enrichment rools: paths toward the comprehensive functional analysis of large gene lists, Nucleic Acids Research 2009 37(1):1-13.
Hummel et al., ProMEX: a mass spectral reference database for proteins and protein phosphorylation sites, BMC Bioinformatics. 2007 8:216.
Kirkpatrick et al., The absolute quantification strategy: a general procedure for the quantification of proteins and post-translational modifications, Methods. 2005 35(3):265-73.
Knebel et al. "A Novel Method to Identify Protein Kinase Substrates: eEF2 Kinase is Phosphorylated and Inhibited by SAPK4/p388." EMBO J. 20.16(2001):4360-4369.
Kubota et al., Sensitive Multiplexed Analysis of Kinase Activities and Activity-based Kinase Identification, Nature Biotechology 2009 27(10):933-940.
Luo et al., Global Impact of Oncogenic Src on a Phosphotyrosine Proteome, J Proteome Res. 2008 7:3447-3460.
Miller et al. "Linear Motif Atlas for Phosphorylation-Dependent Signaling." Sci. Signal. 1.35(2008):ra2.
Montoya et al., Characterization of a TiO2 enrichment method for label-free quantitative phosphoproteomics, Methods 2011 54:370.
Nita-Lazer et al., Quantitative phosphoproteomics by mass spectrometry: past, present, and future, Proteomics. 2008 8 (21):4433-43.
Olsen et al., Global, in vivo, and site-specific phosphorylation dynamics in signaling networks, Cell 2006 127:635-648.
Pasa-Tolic et al., Proteomic analyses using an accurate mass and time tag strategy, Biotechniques. 2004 37(4):621-4.
Perkins et al., Probability-based protein identification by searching sequence databases using mass spectrometry data, Electrophoresis 1999, 20:3551-3567.
Ross et al., Multiplexed protein quantitation in *Saccharomyces cerevisiae* using amine-reactive isobaric tagging reagents, Molecular & Cellular Proteomics 2004 3(12):1154-1169.
Ruse et al., Quantitative dynamics of site-specific protein phosphorylation determined using liquid chromatography electrospray ionization mass spectrometry, Anal Chern. 2002 74(7):1658-64.
Savitski et al. "Confident Phosphorylation Site Localization Using the Mascot Delta Score." Technol. in nov. Resources. 10(2011):1-12.
Schwartz et al., An interative statistical approach to the identification of protein phosphorylation motifs from large-scale data sets, Nature Biotechnology 2005 23(11):1391.
Smith et al., Recent developments in mass spectrometry-based quantitative phosphoproteomics, Biochem Cell Biol. 2008 86(2):137-48.
Steen et al., Stable isotope-free relative and absolute quantitation of protein phosphorylation stoichiometry by MS, PNAS 2005 102(11):3948-53.
Thingholm et al., Analytical strategies for phosphoproteomics, Proteomics 2009 9:1451-1468.
Wang et al., SEMI-quantitation Strategy for Label-free Quantitative Profiling of Phosphoproteome in Lung Cancer of Different Invasive Potential, Proceedings of the 56th ASMS Conference on Mass Spectrometry and Allied Topics, Denver, CO, Jun. 1-5, 2008.
Yang et al., Applying a targeted label-free approach using LC-MS AMT tags to evaluate changes in protein phosphorylation following phosphatase inhibition, J Proteome Res. 2007 6(11):4489-97.
Yi et al., Quantification of phosphorylation of insulin receptor substrate-1 by HPLC-ESI-MS/MS, J Am Soc Mass Spectrom. 2006 17(4):562-7.
Yu et al., A site-specific, multiplexed kinase activity assay using stable-isotope dilution and high-resolution mass spectrometry, PNAS 2009 106(28):11606-11611.
Zhang et al., Targeting cancer with small molecule kinase inhibitors, Nature Reviews Cancer 2009 9:28.
Zhou et al., A systematic approach to the analysis of protein phosphorylation, Nat Biotech. 2001 19(4):375-8.

\* cited by examiner

METHODS FOR QUANTIFYING ACTIVITY OF PROTEIN MODIFYING ENZYMES

FIELD OF THE INVENTION

The present invention relates to a method of quantifying the activity of a protein modifying enzyme and finds particular use in the quantification of the activity of a protein kinase.

BACKGROUND TO THE INVENTION

Lipid and protein kinases mediate cell signalling processes that are important for normal and disease biology. Large-scale phosphoproteomics, now routine in many mass spectrometry (MS) laboratories, should allow the quantification of signalling without a preconception of the routes within the network that may be active. Several thousand phosphorylation sites can now be measured with high accuracy by the use of quantitative techniques based on MS (Thingholm et al, *Proteomics* 9, 1451 (March 2009)).

Since, by definition, each phosphorylation site is the result of a kinase activity (opposed by a phosphatase activity), it should in theory be possible to use phosphoproteomics data to obtain an estimate of activity for each kinase expressed in the system under investigation (Cutillas & Jorgensen, *Biochem J* 434 (March 2011)). This would entail measuring known kinase substrates (i.e., specific phosphorylation sites) which could then be taken as markers of activities of such kinases. However, using phosphoproteomics data to infer the activities of kinases is not straightforward. Databases of substrate-kinase relationships are publically available and, although not comprehensive, a subset of the sites quantifiable by large-scale phosphoproteomics is represented in these databases. The challenge in using this information is that several different kinases may phosphorylate the same substrates and proteins phosphorylated in one cell type may not be expressed or be poor substrates in others. In addition, the dynamic nature of protein phosphorylation means that this modification can quickly change during the course of an experiment and variables difficult to control such as the circadian clock, cell confluence and shear stress introduced as a result of handling cell cultures can all affect protein kinase activity, thus contributing to noisy phosphoproteomics data. Thus because of stochastic effects, a phosphoproteomics experiment may show inconsistent levels of phosphorylation of the known substrate markers of a given kinase activity.

There is therefore a need in the art for a method to reliably infer protein kinase activity based on MS-based phosphoproteomics.

SUMMARY OF THE INVENTION

The present inventors have identified for the first time a way of analysing data obtained from MS-based phosphoproteomics experiments in order to infer the activity of protein modifying enzymes, for example the activity of protein kinases.

Accordingly, in a first aspect the present invention provides a method of quantifying the activity of a protein modifying enzyme in a sample, comprising:

(i) grouping modified peptides from a first sample and modified peptides from a second sample into a single group according to one of the following parameters:

(a) modified peptides having a modification site that is modified by the same protein modifying enzyme; or (b) modified peptides having a modification site that is part of the same modification motif;

(ii) calculating enrichment of the modified peptides from the first sample compared to the modified peptides from the second sample in the group; and (iii) calculating the statistical significance of said enrichment;

wherein a statistically significant enrichment is indicative of a protein modifying enzyme being activated in the first sample compared to the second sample.

DETAILED DESCRIPTION OF THE INVENTION

The present invention relates to a method for quantifying the activity of protein modifying enzymes such as protein kinases in a sample. The method is based on the analysis of modified peptides, for example phosphorylated peptides, which are identified using MS-based techniques.

As described herein, the method of the invention is a method for quantifying the activity of a protein modifying enzyme in a sample. Most proteins are modified in some way by the addition of functional groups and such modifications are effected by protein modifying enzymes. Protein modifications that can be detected by mass spectrometry include phosphorylation, glycosylation, acetylation, methylation and lipidation. These protein modifications have various biological roles in the cell. By "protein modifying enzyme" is therefore meant an enzyme which catalyses a reaction involving the addition of a functional group to a protein or peptide.

The method of the invention can be applied to the quantification of the activity of any protein modifying enzyme whose activity can be detected using MS-based methods. Such enzymes include protein kinases, protein glycosyltransferases, protein acetyltransferases, protein methyltransferases and protein palmitoyltransferases. The activity of these enzymes results in phosphorylation, acetylation, glycosylation, methylation and lipidation of protein or peptide substrates respectively. All of these protein modifications can be detected by mass spectrometry.

In one embodiment, the method of the invention is a method of quantifying the activity of a protein kinase. In this embodiment, the method is based on the analysis of phosphorylated peptides. Phosphorylated peptides contain one or more amino acid which is phosphorylated (i.e. a phosphate ($PO_4$) group has been added to that amino acid). Such phosphorylated amino acids are referred to herein as "phosphorylation sites". In relation to this embodiment of the invention, the term "phosphoprotein" is used herein to refer to a phosphorylated protein and the term "phosphopeptide" is used herein to refer to a phosphorylated peptide.

Human protein kinases can be divided into a number of groups including AGC kinases, for example protein kinase A (PKA), protein kinase B (PKB) (also known as Akt), protein kinase C (PKC) and protein kinase G (PKG); tyrosine kinases; tyrosine-kinase like kinases; calcium/calmodulin-dependent protein kinases; the casein kinase 1 group; CMGC group, for example CDK, MAPK, GSK3 and CLK kinases; and STE, the homologues of yeast Sterile 7, Sterile 11, and Sterile 20 kinases.

The method of the invention is a method of quantifying the activity of a protein modifying enzyme in a sample and involves making a comparison between modified peptides from a first sample and modified peptides from a second sample. The first and second samples used in the methods of the invention can be any samples which contain peptides.

The sample is typically a biological sample and can thus be any type of sample obtained from a biological source, for example a sample obtained from a human, animal, plant or bacterium. The invention thus encompasses the use of samples obtained from human and non-human sources.

The samples used in the methods of the present invention can be from any species of interest. Typically, the samples are from a human or animal. The animal is typically a mammal, for example a rodent such as a mouse, rat or guinea pig, or an ungulate such as a cow, sheep or goat. The animal is alternatively a bird, such as a chicken, a fish, such as a zebra fish, a nematode, such as the worm *Caenorhabditis elegans*, or an insect, such as the fruit fly *Drosophila melanogaster*. The samples used in the methods of the invention can also be from other life-forms such as bacteria and yeast. The samples used in the methods of the invention are typically samples from an experimentally important species of bacterium such as *Escherichia coli, Salmonella enterica, Streptococcus pneumoniae* or *Staphylococcus aureus*, or of yeast such as the baker's yeast *Saccharomyces cerevisiae* or the fission yeast *Schizosaccharomyces pombe*. The samples used in the methods of the invention can alternatively be from a plant or fungus or a virus.

Typically, the biological sample is derived from a human, and can be, for example, a sample of a bodily fluid such as urine or blood, or another tissue. Typically, the biological sample is a cell line or a tissue, typically a primary tissue. For example, the sample can be a tissue from a human or animal. The human or animal can be healthy or diseased. Alternatively, the sample can be a cell line derived from healthy or diseased human or animal cells.

The method of the invention is an in vitro method and therefore does not comprise the step of obtaining a sample from an organism such as an animal.

In a first step (i), the method of the invention comprises grouping modified peptides from a first sample and modified peptides from a second sample into a single group according to one of the following parameters:
  (a) modified peptides having a modification site that is modified by the same protein modifying enzyme; or
  (b) modified peptides having a modification site that is part of the same modification motif.

By "grouping" is meant that modified peptides such as phosphorylated peptides are placed into a group or set. In the method of the invention, modified peptides from a first sample and modified peptides from a second sample are placed into a single group based on one of the parameters (a) and (b) set out above. In the Examples herein, the group is also referred to as a "substrate group". Similarly, a modified peptide is also referred to herein as a "substrate".

In one embodiment, the modified peptides are placed into a group on the basis that they have a modification site that is modified by the same protein modifying enzyme. Thus, each modified peptide in the group has at least one modification site that is modified by the same protein enzyme. For example, phosphorylated peptides are placed into a group on the basis that they have a phosphorylation site that is phosphorylated by the same kinase. In this embodiment, a phosphorylation site within each of the phosphorylated peptides in the group is known to be phosphorylated by the same specific kinase. Similarly, if the protein modifying enzyme is an acetylase, the modified peptides are placed into a group on the basis that they have an acetylation site that is acetylated by the same acetylase. In this embodiment, an acetylation site within each of the acetylated peptides in the group is known to be acetylated by the same specific acetylase.

Information on kinase-substrate relationships and therefore on phosphorylation sites that are phosphorylated by a particular kinase can be obtained from publically available databases, for example PhosphoSite (Hornbeck et al, *Proteomics* 4, 1551 (June 2004)) and PhosphoElm (Dinkel et al, *Nucleic Acids Res* 39, D261 (January 2011)). Similarly, information on other modification sites can be obtained from publically available databases and from individual research papers obtained from the literature.

In another embodiment, the modified peptides are placed into a group on the basis that they have a modification site that is part of the same modification motif. For example, phosphorylated peptides are placed into a group on the basis that they have a phosphorylation site that is part of the same phosphorylation motif. By "modification motif" is meant a specific sequence of amino acids which is modified in the same position by the same enzyme. For example, a "phosphorylation motif" is a specific sequence of amino acids which is phosphorylated in the same position by the same protein kinase or by functionally related kinases. In this embodiment, a phosphorylation site within each of the phosphorylated peptides in the group is part of a predefined phosphorylation motif.

Information on modification motifs such as phosphorylation motifs can be obtained, for example, from the literature or from an analysis of a dataset using a computer programme such as Motif-X (Schwartz and Gygi, *Nat Biotechnol* 23, 1391 (November 2005)).

When the protein modifying enzyme is a protein kinase, step (i) of the method of the invention comprises grouping phosphorylated peptides from a first sample and phosphorylated peptides from a second sample into a single group according to one of the following parameters:
  (a) phosphorylated peptides having a phosphorylation site that is phosphorylated by the same protein kinase; or
  (b) phosphorylated peptides having a phosphorylation site that is part of the same phosphorylation motif;

Prior to grouping the modified peptides, modified peptides can be selected for use in the method of the invention according to statistical significance of the occurrence of the modification.

The method of the invention involves grouping modified peptides from a first sample and from a second sample into a single group. The present invention therefore finds use in the comparison of the activity of a protein modifying enzyme such as a protein kinase between at least two samples, for example the comparison of two samples that are from different sources or which have been treated with different test substances. Alternatively, the method of the invention can be used to compare a test sample and a control sample. In this embodiment, one of the two samples is a control sample. In this embodiment, the first and second sample can be from the same source but either the first or second sample is treated with a test substance whilst the other sample is not treated in this way.

In one embodiment, the method of the invention is used to compare the activity of a protein modifying enzyme such as a protein kinase between more than two samples, for example 3, 4, 5, 6, 7, 8, 9, 10 or even more samples. In this embodiment, step (i) of the method of the invention involves grouping modified peptides from all of the samples into a single group according to one of the parameters (a) and (b) as described herein. Steps (ii) and (iii) of the method of the invention are then carried out to compare enrichment of the modified peptides from one of the samples compared to the modified peptides from another sample in the group. For example, when there are 3 samples, enrichment of modified peptides in the first versus the second sample, in the second verses the third sample and in the first versus the third sample can be compared.

In some embodiments of the invention, the sample itself or the organism from which the sample is obtained is treated with a test substance prior to carrying out the method of the invention. Thus, in this embodiment, a cell line or an organism from which a tissue is obtained is treated with a test substance prior to carrying out the method of the invention. The test substance is typically an exogenous chemical or drug, such as small molecule inhibitors, RNAi, therapeutic peptides, and antibodies. This embodiment of the invention allows the investigation of the effects of the test substance on the activity of a protein modifying enzyme and the comparison of such effects on different samples.

For example, in one embodiment, a cell line can be treated with agonists of pathways and/or kinase inhibitors prior to carrying out the method of the invention. Typical kinase inhibitors include inhibitors of src and phosphoinositide 3-kinase (PI3K), such as PP2 and PI-103. Other inhibitors of PI3K include wortmannin. At least 80 kinase inhibitors are in different stages of clinical development (Zhang, J.; et al *Nat Rev Cancer* 2009, 9, (1), 28-39). The technique is also useful to investigate other types of inhibitors suspected to have an effect on kinase pathways, such as HSP90 inhibitors, phosphatase inhibitors and antibody drugs.

A "peptide" as defined herein is a short amino acid sequence and includes oligopeptides and polypeptides. Typically, such peptides are between about 5 and 30 amino acids long, for example from 6 or 7 to 25, 26 or 27 amino acids, from 8, 9 or 10 to 20 amino acids, from 11 or 12 to 18 amino acids or from 14 to 16 amino acids, for example 15 amino acids. However, shorter and longer peptides, such as between about 2 and about 50, for example from about 3 to about 35 or 40 or from about 4 to about 45 amino acids can also be used. Typically, the peptide is suitable for mass spectrometric analysis, that is the length of the peptide is such that the peptide is suitable for mass spectrometric analysis. The length of the peptide that can be analysed is limited by the ability of the mass spectrometer to sequence such long peptides. In certain cases polypeptides of up to 300 amino acids can be analysed, for example from 50 to 250 amino acids, from 100 to 200 amino acids or from 150 to 175 amino acids.

As described herein, the method of the invention is based on the analysis of modified peptides identified using MS-based techniques. Accordingly, the modified peptides from a first sample and from a second sample which are grouped in the first step of the method of the invention are typically identified and/or quantified using MS-based techniques. In some embodiments, the method of the invention therefore includes a step of identifying modified peptides in a first sample and/or a second sample using mass spectrometry (MS), prior to the step (i) of grouping the modified peptides from a first sample and from a second sample. In this embodiment, the invention provides a method of quantifying the activity of a protein modifying enzyme in a sample, comprising identifying modified peptides in a first sample and a second sample using mass spectrometry (MS) and:

(i) grouping modified peptides from a first sample and modified peptides from a second sample into a single group according to one of the following parameters:
  (a) modified peptides having a modification site that is modified by the same protein modifying enzyme; or
  (b) modified peptides having a modification site that is part of the same modification motif;

(ii) calculating enrichment of the modified peptides from the first sample compared to the modified peptides from the second sample in the group; and (iii) calculating the statistical significance of said enrichment;

wherein a statistically significant enrichment is indicative of a protein modifying enzyme being activated in the first sample compared to the second sample.

Identification and quantification of modified peptides can be carried out using any suitable method. Typically, quantification can be carried out by any method involving mass spectrometry (MS), such as liquid chromatography-mass spectrometry (LC-MS). The LC-MS or LC-MS/MS is typically label-free MS but techniques that use isotope labelling as the basis for quantification can also be used as the basis for the analysis.

In the methods of the present invention, quantification of a protein modification such as phosphorylation is typically carried out using the TIQUAS (targeted and in-depth quantification of signalling) technique, as described in WO 2010/119261 (International patent application no. PCT/GB2010/000770) and incorporated herein in its entirety by reference. This technique allows for sensitive, rapid and comprehensive quantification of modified peptides. The method can, in one simple assay, simultaneously measure the amounts of thousands of phosphorylation sites on proteins. As set out in WO 2010/119261, the TIQUAS technique can also be used to quantify modified peptides other than phosphorylated peptides. In fact, the TIQUAS technique can be used to quantify peptides which contain any modifications which can be detected by mass spectrometry.

In this embodiment of the method of the invention, the step of identifying modified peptides using mass spectrometry (MS) prior to step (i) is carried out using a method comprising the following steps:
  (a) obtaining peptides from a sample;
  (b) adding reference modified peptides to the peptides obtained in step (a) to produce a mixture of peptides and reference modified peptides;
  (c) carrying out mass spectrometry (MS) on said mixture of peptides and reference modified peptides to obtain data relating to the peptides in the sample; and
  (d) comparing the data relating to the peptides in the sample with data in a database of modified peptides using a computer programme;
wherein the database of modified peptides is compiled by a method comprising:
  i obtaining peptides from a sample;
  ii enriching modified peptides from the peptides obtained in step i;
  iii carrying out liquid chromatography-tandem mass spectrometry (LC-MS/MS) on the enriched modified peptides obtained in step ii;
  iv comparing the modified peptides detected in step iii to a known reference database in order to identify the modified peptides; and
  v compiling data relating to the modified peptides identified in step iv into a database.

In one embodiment of the method of the invention, where the protein modifying enzyme is a protein kinase and the modification is phosphorylation, the step of identifying modified peptides using mass spectrometry (MS) prior to step (i) is carried out using a method comprising the following steps:
  (a) obtaining phosphorylated peptides from a sample;
  (b) adding reference phosphorylated peptides to the peptides obtained in step (a) to produce a mixture of peptides and reference phosphorylated peptides;

(c) carrying out mass spectrometry (MS) on said mixture of peptides and reference phosphorylated peptides to obtain data relating to the peptides in the sample; and (d) comparing the data relating to the peptides in the sample with data in a database of phosphorylated peptides using a computer programme;

wherein the database of phosphorylated peptides is compiled by a method comprising:

i obtaining peptides from a sample;

ii enriching phosphorylated peptides from the peptides obtained in step i;

iii carrying out liquid chromatography-tandem mass spectrometry (LC-MS/MS) on the enriched phosphorylated peptides obtained in step ii;

iv comparing the phosphorylated peptides detected in step iii to a known reference database in order to identify the phosphorylated peptides; and v compiling data relating to the phosphorylated peptides identified in step iv into a database.

In relation to this embodiment of the invention, the work "peptide" is used interchangeably with the word "polypeptide".

Step (a) of this embodiment of the invention involves obtaining peptides from a sample. Peptides can be obtained from the sample using any suitable method known in the art. In one embodiment, step (a) of the method of the invention comprises:

(1) lysing cells in the sample;

(2) extracting the proteins from the lysed cells obtained in step (1); and (3) cleaving said proteins into peptides.

In step (1) of this embodiment of the invention, the cells in the sample are lysed, or split open. The cells can be lysed using any suitable means known in the art, for example using physical methods such as mechanical lysis (for example using a Waring blender), liquid homogenization, sonication or manual lysis (for example using a pestle and mortar) or detergent-based methods such as CHAPS or Triton-X. Typically, the cells are lysed using a denaturing buffer such as a urea-based buffer.

In step (2) of this embodiment of the invention, proteins are extracted from the lysed cells obtained in step (1). In other words, the proteins are separated from the other components of the lysed cells.

In step (3) of this embodiment of the invention, the proteins from the lysed cells are cleaved into peptides. In other words, the proteins are broken down into shorter peptides. Protein breakdown is also commonly referred to as digestion. Protein cleavage can be carried out in the present invention using any suitable agent known in the art.

Protein cleavage or digestion is typically carried out using a protease. Any suitable protease can be used in the present invention. In the present invention, the protease is typically trypsin, chymotrypsin, Arg-C, pepsin, V8, Lys-C, Asp-C and/or AspN. Alternatively, the proteins can be cleaved chemically, for example using hydroxylamine, formic acid, cyanogen bromide, BNPS-skatole, 2-nitro-5-thiocyanobenzoic acid (NTCB) or any other suitable agent.

In step (b) of this embodiment, reference modified peptides (typically reference phosphorylated peptides) are added to the peptides obtained in step (a) to produce a mixture of peptides and reference modified peptides (typically reference phosphorylated peptides). Step (b) thus results in one mixture of peptides (including modified ones, typically phosphorylated ones) per sample. The reference modified peptides (typically reference phosphorylated peptides) are also referred to herein as "internal standards" (ISs). Typically, 5 to 10, for example 6 to 9 or 7 to 8, reference modified peptides (typically reference phosphorylated peptides) are added.

In the present invention, the reference modified peptides are typically reference phosphorylated peptides and are typically derived from a reference protein of defined nature and concentration, often referred to as an internal standard (IS) protein. ISs can be commercially available proteins, for example casein. Alternatively, ISs are synthesised specifically for use in the invention. In this embodiment of the invention, reference phosphorylated peptides are typically synthesised with the same sequence as some of the phosphorylated peptides that it is desired to quantify but which are enriched in stable heavy isotopes of carbon and nitrogen. The peptides are typically synthesised using solid phase chemistry in which one amino acid is added at a time to form an amino acid chain or polypeptide. Typically, such peptides are enriched in $^{13}$C and $^{15}$N that substitute the common $^{12}$C and $^{14}$N. This enrichment results in the reference phosphorylated peptides being approximately 6 to 10 daltons heavier than the endogenous phosphorylated peptides with the same sequence so that they can be distinguished using a mass spectrometer.

In another embodiment of the invention, when the protein modifying enzyme is a protein acetyltransferase and acetylated peptides are being quantified, the reference modified peptides are reference acetylated peptides. Such reference acetylated peptides are typically synthetic peptides containing acetylated amino acids.

The reference modified peptides (typically reference phosphorylated peptides) are typically added at a known amount in each of the samples to be compared. The signals of the endogenous modified peptides (typically phosphorylated peptides) are normalised to the signal of the reference modified peptides (typically reference phosphorylated peptides) in downstream analysis.

In one embodiment, step (b) of this embodiment further comprises enriching modified peptides (typically phosphorylated peptides) from the mixture of peptides and reference modified peptides (typically reference phosphorylated peptides) obtained in step (b) to produce a mixture of enriched modified peptides (typically phosphorylated peptides). This additional step thus results in a single mixture of enriched modified peptides (typically phosphorylated peptides) per sample. In this embodiment of the invention, step (c) thus comprises carrying out mass spectrometry (MS) on the mixture of enriched modified peptides (typically phosphorylated peptides) to obtain data relating to the peptides in the sample. In this embodiment of the invention, step (b) typically results in a mixture of enriched modified peptides (typically phosphorylated peptides).

The step of enriching modified peptides (typically phosphorylated peptides) is typically carried out using chromatography. In one embodiment, the chromatography is immobilized metal ion affinity chromatography (IMAC), titanium dioxide ($TiO_2$) chromatography, and/or zirconium dioxide ($ZrO_2$) chromatography. Typically, the chromatography is IMAC and $TiO_2$ chromatography.

Alternatively, the step of enriching modified peptides (typically phosphorylated peptides) is carried out using antibody-based methods.

In one embodiment of the invention, when the protein modifying enzyme is a protein kinase and the peptides being quantified are phosphorylated peptides, antibodies with affinity to phosphorylated amino acids such as tyrosine, threonine, serine or histidine are linked (immobilised) to a solid matrix. Phosphorylated peptides are enriched by the ability of these antibodies to specifically bind phosphorylated peptides. Non-phosphorylated peptides are then washed away while phosphorylated peptides are retained on the antibody coated matrices. Elution of phosphorylated peptides from the immobilised antibody is typically carried out using low pH solvents or by any other suitable method that denatures the interaction between antibody and phosphorylated peptides.

In another embodiment of the invention, when the protein modifying enzyme is a protein acetyltransferase and the peptides being quantified are acetylated peptides, acetylated peptides are enriched by the use of specific antibodies against acetylated amino acid residues. Such antibodies are linked to a solid matrix and then enriched by the ability of the antibodies to specifically bind acetylated amino acid residues. Non-acetylated peptides are then washed away while acetylated peptides are retained on the immobilised antibody.

In step (c) of this embodiment, mass spectrometry (MS) is carried out on the mixture of peptides and reference modified peptides (typically reference phosphorylated peptides) obtained in step (b) to obtain data relating to the peptides in the sample. Typically, this data is in the form of an MS datafile for the sample. In one embodiment of the invention, when step (b) of this embodiment further comprises enriching modified peptides (typically phosphorylated peptides) from the mixture of peptides and reference modified peptides (typically reference phosphorylated peptides) obtained in step (b) to produce a mixture of enriched modified peptides (typically phosphorylated peptides), step (c) comprises carrying out mass spectrometry (MS) on said mixture of enriched modified peptides (typically phosphorylated peptides) to obtain data relating to the peptides in the sample, typically an MS datafile for the sample. Typically, the mass spectrometry is liquid chromatography-mass spectrometry (LC-MS). Step (c) thus typically results in an LC-MS datafile (one from each sample).

The data relating to the peptides in the sample typically comprises the mass to charge (m/z) ratio, charge (z) and/or relative retention time of the peptides.

In step (d) of this embodiment, the data relating to the peptides in the sample (typically in the form of an MS datafile and more typically an LC-MS datafile) is compared with data in a database of modified peptides (typically phosphorylated peptides) using a computer programme. For example, the mass to charge (m/z) ratio, charge (z) and relative retention time of the peptides in the sample are compared with the mass to charge (m/z) ratio, charge (z) and relative retention time of the modified peptides (typically phosphorylated peptides) in the database. This enables the identification and quantification of each modified peptide (typically phosphorylated peptide) in the sample using the database of modified peptides (typically phosphorylated peptides).

Typically, the computer programme is the programme termed PESCAL (Cutillas, P. R.; Vanhaesebroeck, B. *Mol Cell Proteomics* 6(9), 1560-73, 2007). PESCAL constructs extracted ion chromatograms (XIC, i.e, an elution profile) for each of the modified peptides (typically phosphorylated peptides) present in the database across all the samples that are to be compared. This is done by centring the XIC on the m/z and retention time of the peptide previously identified to be modified (typically phosphorylated) (i.e, present in the database constructed in the first step of the procedure). PESCAL also considers the charge of the peptide to help in the correct assignment of identity. The program also calculates the peak height and area under the curve of each XIC. The data is normalised by dividing the intensity reading (peak areas or heights) of each modified peptides (typically phosphorylated peptide) that is being analysed by those of the reference modified peptides (typically reference phosphorylated peptides).

In this embodiment, the database of modified peptides is compiled by a method comprising the following steps:
 i obtaining peptides from a sample;
 ii enriching modified peptides from the peptides obtained in step i;
 iii carrying out liquid chromatography-tandem mass spectrometry (LC-MS/MS) on the enriched modified peptides obtained in step ii;
 iv comparing the modified peptides detected in step iii to a known reference database in order to identify the modified peptides; and
 v compiling data relating to the modified peptides identified in step iv into a database.

Step i of this embodiment involves obtaining peptides from a sample. Peptides can be obtained from the sample using any suitable method known in the art and as described herein.

The sample is typically a biological sample and can thus be any type of sample obtained from a biological source, as described above. Typically, the sample is a cell line or a tissue.

In some embodiments of the invention, where the sample used in step i is a cell line, the sample is treated with an inhibitor prior to carrying out step i. The inhibitor can be any suitable type of inhibitor. Typically, when phosphorylated peptides are being quantified, the inhibitor is a phosphatase inhibitor. Treatment with phosphatase inhibitors increases the stoichiometry of phosphorylation and results in a greater number of phosphorylated peptides that can be included in the database. In addition, methyl transferase or acetyl hydrolase inhibitors can be used when the purpose is to quantify methylated and acetylated peptides, respectively.

In one embodiment, step i of this embodiment of the method of the invention comprises:
 (1) lysing cells in a sample;
 (2) extracting the proteins from the lysed cells obtained in step (1); and
 (3) cleaving said proteins into peptides.

These aspects of the invention are as described above. However, step (3) is typically carried out using the same method as in step (a) described above.

In step ii of this embodiment, modified peptides (typically phosphorylated peptides) are enriched from the peptides obtained in step i. Step ii thus results in several fractions enriched in modified peptides (typically phosphorylated peptides).

The enrichment of modified peptides (typically phosphorylated peptides) in step ii is typically carried out using multidimensional chromatography. In one embodiment, the multidimensional chromatography is carried out using strong cation exchange high performance liquid chromatography (SCX-HPLC), immobilized metal ion affinity chromatography (IMAC) and titanium dioxide ($TiO_2$) chromatography. In another embodiment, the multidimensional chromatography is carried out using anion exchange high performance liquid chromatography (SAX-HPLC), immobilized metal ion affinity chromatography (IMAC) and titanium dioxide ($TiO_2$) chromatography. In these embodiments of the invention, the chromatographical techniques are carried out sequentially.

Alternatively, the enrichment of modified peptides (typically phosphorylated peptides) in step ii is carried out using antibody-based methods, as described above.

In step iii of this embodiment, liquid chromatography-tandem mass spectrometry (LC-MS/MS) is carried out on the enriched modified peptides (typically phosphorylated peptides) obtained in step ii.

In step iv of this embodiment, the modified peptides (typically phosphorylated peptides) detected in step iii are compared to a known reference database in order to identify the modified peptides (typically phosphorylated peptides). This step is typically carried out using a commercially available search engine, such as, but not restricted to, the MASCOT, ProteinProspector, or Sequest search engines.

In step v of this embodiment, data relating to the modified peptides (typically phosphorylated peptides) identified in step iv is compiled into a database. This database lists all the parameters needed for the quantification of phosphorylated peptides in subsequent biological experiments. Typically, the data relating to the modified peptides (typically phosphorylated peptides) includes identity of the modified peptides (typically phosphorylated peptide), mass to charge (m/z) ratio, charge and/or relative retention time. This allows data relating to the peptides in the sample, typically the mass to charge (m/z) ratio, charge (z) and relative retention time of the peptides in the sample, to be compared to the values for the modified peptides (typically phosphorylated peptides) in the database and thus allows the identification and quantification of the modified peptides (typically phosphorylated peptides) in the sample.

In this embodiment, the compilation of the database does not need to be carried out simultaneously with the method of the invention. The compilation of the database can be carried out separately, in advance of the TIQUAS technique being used in the method of the invention to identify the peptide in the sample.

The basis of the TIQUAS technique is the construction of a database of modified peptides (typically phosphorylated peptides) that can be detected and quantified by LC-MS. This database lists all the parameters needed for the quantification of modified peptides (typically phosphorylated peptides) in subsequent biological experiments including the identity of the modified peptide (typically phosphorylated peptide), mass to charge ratio (m/z), charge, and relative retention time. The database can be constructed by enriching modified peptides (typically phosphorylated peptides) using multidimensional chromatography (such as strong cation exchange, IMAC and $TiO_2$). Fractions of enriched modified peptides (typically phosphorylated peptides) can then be analysed by LC-MS/MS for identification of modified peptides (typically phosphorylated peptides).

The computer program named PESCAL (Cutillas and Vanhaesebroeck, *Molecular & Cellular Proteomics* 6, 1560-1573 (2007)) automates the quantification of each of the modified peptides (typically phosphorylated peptides) listed in the database in LC-MS runs of modified peptides (typically phosphorylated peptides) taken from biological experiments. For these biological experiments, proteins in cell lysates are digested using trypsin or other suitable proteases. Peptide (such as phosphopeptide) internal standards, which are reference modified peptides (typically reference phosphorylated peptides), are spiked at known amounts in all the samples to be compared.

Modified peptides (typically phosphorylated peptides) in the resultant peptide mixture are enriched using a simple-to-perform IMAC or $TiO_2$ extraction step. Enriched modified peptides (typically phosphorylated peptides) are analysed in a single LC-MS run of typically but not restricted to about 120 minutes (total cycle). PESCAL then constructs extracted ion chromatograms (XIC, i.e, an elution profile) for each of the modified peptides (typically phosphorylated peptides) present in the database across all the samples that are to be compared. The program also calculates the peak height and area under the curve of each XIC. The data is normalised by dividing the intensity reading (peak areas or heights) of each modified peptide (typically phosphopeptide) analyte by those of the modified peptide (typically phosphopeptide) ISs.

As an alternative to using the TIQUAS technique, in the methods of the invention, quantification of modifications such as phosphorylation can also be carried out using MS techniques that use isotope labels for quantification, such as metabolic labeling (e.g., stable isotope labeled amino acids in culture, (SILAC); Olsen, J. V. et al. *Cell* 127, 635-648 (2006)), and chemical derivatization (e.g., iTRAQ (Ross, P. L.; et al. *Mol Cell Proteomics* 2004, 3, (12), 1154-69), ICAT (Gygi, S. P. et al. *Nat Biotechnol* 17, 994-999 (1999)), TMT (Dayon L et al, Anal Chem. 2008 Apr. 15; 80(8):2921-31) techniques. In the methods of the invention, protein modifications can be quantified with LC-MS techniques that measure the intensities of the unfragmented ions or with LC-MS/MS techniques that measure the intensities of fragment ions (such as Selected Reaction Monitoring (SRM), also named multiple reaction monitoring (MRM)).

Once the modified peptides have been grouped according to one of the parameters (a) and (b) described herein, the next step in the method of the invention is (ii) calculating enrichment of the modified peptides from the first sample compared to the modified peptides from the second sample in the group.

By "enrichment" of the modified peptides is meant an increase in abundance or frequency. Accordingly, in this step of the method of the invention the increase in abundance or frequency of the modified peptides from the one sample (the first sample) is compared to the increase (or decrease) in abundance or frequency of the modified peptides from another sample (the second sample). As set out above, when more than two samples are being used in the method of the invention, this step is carried out to compare enrichment of modified peptides between any two of the samples at a time. Calculation of enrichment can be done using any appropriate method.

In one embodiment, enrichment is calculated by counting the number of modified peptides in the group which are more abundant in the first sample than in the second sample and the number of modified peptides in the group which are less abundant in the first sample than in the second sample; and subtracting the number of modified peptides in the group which are less abundant in the first sample than in the second sample from the number of modified peptides in the group which are more abundant in the first sample than in the second sample. This can alternatively be worded as subtracting the number of modified peptides in the group which are more abundant in the second sample than in the first sample from the number of modified peptides in the group which are more abundant in the first sample than in the second sample.

This method therefore involves counting the number of modified peptides in the group from the first sample whose intensities are increased or decreased relative to the second sample. In some embodiments, only modified peptides in the group from the first sample whose intensities are statistically significantly increased or decreased relative to the second sample are taken into account. The enrichment of modified peptides is then calculated by a parameter referred to herein as "delta counts", which is defined as the number of modified peptides in a substrate group that increase their intensity relative to second sample minus those that decrease their intensity. The advantage of this approach is that it does not involve divisions and therefore it is applicable to situations where the number of modified peptides in a particular group is zero in some of the samples being compared. An example of this approach is shown in FIG. 6B.

In another embodiment, enrichment is calculated by comparing the mean abundance of all of the modified peptides in the group from the first sample to the mean abundance of all of the modified peptides in the group from the second sample. This is typically done by calculating the mean (arithmetic average) abundance of all the modified peptides in the group from the first sample and the mean abundance of all of the modified peptides in the group from the second sample; and dividing the mean abundance of all of the modified peptides in the group from the first sample by the mean abundance of all of the modified peptides in the group from the second sample. The resultant figure can optionally be log 2 transformed. This method therefore involves comparing the means (arithmetic average) of the intensities of all the modified peptides in the group from a first sample relative to intensities of all the modified peptides in the group from the second sample. An example of this approach is shown in FIG. 6A. This is referred to herein as the "fold" method.

In another embodiment, enrichment is calculated by calculating the mean of all fold changes of the modified peptides in the group and the mean of all fold changes of the modified peptides across the whole experiment; and then dividing the mean of all fold changes of the modified peptides in the group by the mean fold change of all of the modified peptides across the whole experiment. The resultant figure can optionally be log 2 transformed. An example of this approach is shown in FIG. 6C. This is referred to herein as the "enrichment" method.

The final step (iii) of the method of the invention comprises calculating the statistical significance of the enrichment. The method of the invention involves calculating the enrichment of the modified peptides from the first sample compared to the modified peptides from the second sample in the group. Accordingly, a statistically significant enrichment in this method is indicative of a protein modifying enzyme being activated in the first sample compared to the second sample. If the enrichment is not statistically significant, this indicates that the protein modifying enzyme is not activated in the first sample. It will be understood that the converse will also apply, i.e. that if there is enrichment of the modified peptides from the second sample compared to the modified peptides from the second sample in the group, then the protein modifying enzyme is activated in the second sample compared to the first sample.

Statistical significance can be calculated using any suitable statistical method, which will be within the capability of a person skilled in the art. Suitable statistical methods include the hypergeometric test, the paired t-test, the Z-test, the Kolmogorov-Smirnov test, Chi-squared test, Fisher's exact test, or the Wilcoxon's signed-rank test. Any of these tests can optionally be followed by a multiple testing correction method such as the Benjamini Hochberg False Discovery Rate (FDR) method.

For example, the significance of enrichment can be calculated by the hypergeometric test. This can optionally be followed by a multiple testing correction method such as the Benjamini Hochberg FDR method. This method of calculating significance is typically used in combination with the "delta counts" method described herein. Alternatively, significance of enrichment can be calculated using the paired t-test. Again, this can optionally be followed by a multiple testing correction such as the Benjamini Hochberg FDR method. This method of calculating significance is typically used in combination with the "fold" method described herein. In the "enrichment" method described herein, statistical significance of enrichment can in one embodiment be calculated using a Z score=(mS−mP)*$m^{1/2}$/δ (where mS: Log 2 mean intensities substrate group; mP: Log 2 mean intensities whole dataset; m: size of substrate group; δ: standard deviation mean intensities whole dataset). The z score can then be converted to a p-value. A statistically significant enrichment can be determined based on a suitable p-value, for example p<0.05, p<0.01 or p<0.001. In some embodiments, statistical significance can be calculated using an appropriate computer programme.

In the method of the invention, a statistically significant enrichment is indicative of a protein modifying enzyme being activated in the first sample compared to the second sample. This can also be described as a differential enrichment of modified peptides between samples. Thus, the method of the invention can be considered as a method for determining differential activation of a protein modifying enzyme such as a kinase in a first sample compared to a second sample. However, quantification of the results can be obtained, for example, by analysing the enrichment using different concentrations of a test substance and observing concentration-dependent effects.

The present inventors have devised a technique to systematically infer protein kinase pathway activation from MS-based phosphoproteomics data. The technique is termed Kinase Substrate Enrichment Analysis (KSEA).

In one embodiment, the method is a method of quantifying protein kinase activity in a sample, comprising:
 (i) grouping phosphorylated peptides from a first sample and phosphorylated peptides from a second sample into a single group according to one of the following parameters:
  (a) phosphorylated peptides having a phosphorylation site that is phosphorylated by the same protein kinase; or
  (b) phosphorylated peptides having a phosphorylation site that is part of the same phosphorylation motif;
 (ii) calculating enrichment of the phosphorylated peptides from the first sample compared to the phosphorylated peptides from the second sample in the group; and
 (iii) calculating the statistical significance of said enrichment;
 wherein a statistically significant enrichment is indicative of a protein kinase being activated in the first sample compared to the second sample.

In one embodiment, enrichment is calculated by counting the number of phosphorylated peptides in the group which are more abundant in the first sample than in the second sample and the number of phosphorylated peptides in the group which are less abundant in the first sample than in the second sample; and subtracting the number of phosphorylated peptides in the group which are less abundant in the first sample than in the second sample from the number of phosphorylated peptides in the group which are more abundant in the first sample than in the second sample.

In another embodiment, enrichment is calculated by calculating the mean (arithmetic average) abundance of all the phosphorylated peptides in the group from the first sample and the mean abundance of all of the phosphorylated peptides in the group from the second sample; and dividing the mean abundance of all of the phosphorylated peptides in the group from the first sample by the mean abundance of all of the phosphorylated peptides in the group from the second sample.

In another embodiment, enrichment is calculated by calculating the mean of all fold changes of the phosphorylated peptides in the group and the mean of all fold changes of the phosphorylated peptides across the whole experiment; and then dividing the mean of all fold changes of the phosphorylated peptides in the group by the mean fold change of all of the phosphorylated peptides across the whole experiment.

The present invention will now be further described by way of reference to the following Examples which are present for the purposes of illustration only. In the Examples, reference is made to a number of Figures in which:

FIGS. 1A, 1B, 1C. 1D. 1E, and 1F show that phosphopeptides are differentially regulated in P31/Fuj and Kasumi-1 cells. P31/Fuj and Kasumi-1 cells were seeded 24 h previous to harvesting and processed for label free MS analysis as described in the Materials and Methods section of the Examples herein. (A) Volcano plot of the fold and p-values for each phosphorylation site showing the phosphopeptide levels in P31/Fuj cells relative to Kasumi-1 cells. Mean refers to the arithmetic average of the Log 2 fold data. (B) Summary of phosphopeptides differentially regulated between P31/Fuj and Kasumi-1 cells. (C) Frequency distribution of fold change in phosphorylation between cell lines. (D) Principal component analysis of P31/Fuj and Kasumi-1 cells based on global phosphorylation data. (E) Illustrative examples of substrate group expression across the two cell lines. Each data point is the Log 2 fold difference of a phosphopeptide containing a phosphorylation site known to be the substrate of the named kinase. (F) Substrate group enrichment data of kinases represented with more than three entries in the substrate group.

FIGS. 2A and 2B show the determination of differentially activated kinases between P31/Fuj and Kasumi-1 cells using kinase-substrate enrichment analysis (KSEA) taking phosSite as the database of kinase-substrate relationships. Phosphopeptides differentially regulated between P31/Fuj and Kasumi-1 cells were used to infer distinctive kinase activity between both cell lines. Kinase activities were inferred using algorithms based on counting phosphopeptides (A) or by comparing the means of phosphopeptide intensities to substrate groups (B).

FIGS. 3A and 3B show the determination of differentially activated kinases between P31/Fuj and Kasumi-1 cells using kinase-substrate enrichment analysis (KSEA) taking phosphoElm as the database of kinase-substrate relationships. Phosphopeptides differentially regulated between P31/Fuj and Kasumi-1 cells were used to infer distinctive kinase activity between both cell lines. Kinase activities were inferred using algorithms based on counting phosphopeptides (A) or by comparing the means of phosphopeptide intensities to substrate groups (B).

Figure 6:
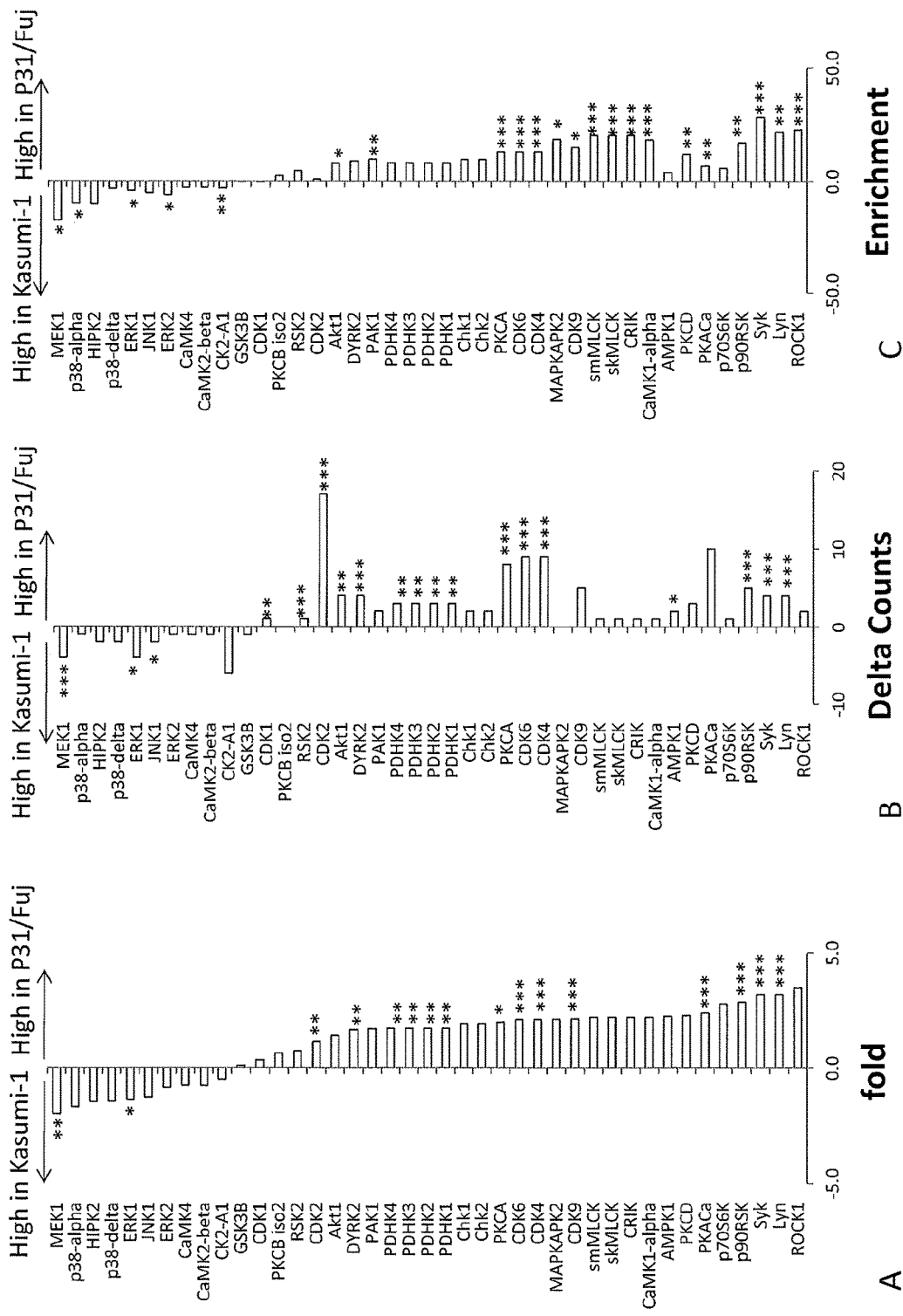

FIGS. 6A, 6B, and 6C show a comparison of enrichment strategies. Three different mathematical methods to infer enrichment of substrate groups into the phosphoprotcomics data were tested. The different values were calculated as follows. (A) Fold=log 2 (mean substrate group intensities in P31-Fuji/mean substrate group intensities in Kasumi-1), Significance of enrichment was calculated by paired t-test in Excel. (B) Delta counts=number of substrates in substrate group significantly increased in P31-Fuj minus those increased in Kasumi-1. Significance of enrichment was calculated by the hypergeometric test in Excel. (C) Enrichment=Log 2 Mean of substrate group divided by Log 2. Mean of all data. The significance of enrichment was calculated using a Z score=$(mS-mP)*m^{1/2}/\delta$ (where mS: Log 2 mean intensities substrate group; mP: Log 2 mean intensities whole dataset; m: size of substrate group; $\delta$: standard deviation mean intensities whole dataset). The z score was converted to a p-value in Excel. Significance of enrichments are denoted as * p<0.05:  p<0.01; * <0.001.

FIGS. 7A, 7B, 7C, 7D, and 7E show the heterogeneity of substrate group enrichment in primary AML blasts. (A) Hierarchical clustering (Spearman correlation, complete linkage) of substrate enrichment values identified 12 main clusters. (B, C) Examples of co-regulated substrate groups (m, number of phosphopeptides quantified in the named substrate group). (D) Negative correlation between activities in cluster 5a and those in clusters 9, 6 and 7 comprising substrates for CK2a, PKB/PKC, PAK/MAPKAPK2, and Lyn/Syk/Tyr, respectively. (E) Kinase substrate groups more frequently enriched across primary AML.

EXAMPLE 1—KINASE SUBSTRATE ENRICHMENT ANALYSIS (KSEA) IN P31/FUJ AND KASUMI-1 CELLS

Materials and Methods

Cell Culture

P31/Fuj and Kasumi-1 cells were grown in RPMI-1640 supplemented with 10% FBS, 100 units/mL penicillin/streptomycin and 50 µM b-Mercaptoethanol at 37 C in a humidified atmosphere at 5% $CO_2$. Cells were maintained at a confluency of 0.5-2×$10^6$ cells/mL.

Cell Lysis and Protein Digestion

Cells were split at a confluency of 0.5×$10^6$ cells/mL and for each condition 3 independent biological replicates were performed per experiment and all experiments were done twice for a total of at least 6 biological replicates per condition. A total of 10×$10^6$ cells per condition were harvested by centrifugation, washed twice with cold PBS supplemented with 1 mM $Na_3VO_4$ and 1 mM NaF and lysed in 1 mL of Urea buffer (8 M Urea in 20 mM Hepes pH 8.0 supplemented with 1 mM $Na_3VO_4$, 1 mM NaF, 1 mM, 1 mM β-glycerophosphate and 1 mM okadaic acid). Cell lysates were further homogenized by sonication (3 pulses of 15 s) and insoluble material was removed by centrifugation. Protein was quantified using the Bradford assay. 0.5 mg of protein per sample were reduced and alkylated by sequencial incubation with 4.1 mM DTT and 8.3 mM Iodoacetamide for 15 min at RT in the dark. For protein digestion, urea concentration was reduced to 2M by adding 20 mM Hepes pH 8.0. Immobilized TLCK-typsin (20 TAME units/mg) was added and samples were incubated overnight at 37° C. Digestion was stopped by adding 1% TFA final concentration and trypsin beads were removed by centrifugation. The resultant peptide solutions were desalted using C18-Oasis cartridges as indicated by the manufacturer with slight modifications. Briefly, Oasis cartridges were conditioned with 1 mL ACN and equilibrated with 1 mL of wash solution (0.1% TFA/2% ACN). Peptides were loaded in the cartridges and washed with 1.5 mL of wash solution. Finally, peptides were eluted with 0.5 mL of glycolic acid buffer (1M glycolic acid/5% TFA/80% ACN).

Phosphopeptide Enrichment

Peptide phosphoenrichment was performed using $TiO_2$ as previously described (Montoya et al, Methods 54, 370, 2011). Briefly, peptide eluents were normalized to 1 mL with glycolic acid buffer and incubated with 25 μL of $TiO_2$ buffer (50% slurry in X % TFA) for 5 min at RT. $TiO_2$ beads were packed by centrifugation in C18 Spin columns previously equilibrated with glycolic acid buffer. Columns were sequentially washed with 300 μL of glycolic acid, 50% ACN and ammonium bicarbonate buffer (20 mM $NH_4HCO_3$ pH 6.8 in 50% ACN). For phosphopeptide elution, beads were incubated for 1 min at RT with 50 μL of 5% $NH_4OH$ in 50% ACN and centrifuged. This step was repeated 3 times. Eluents from the same sample were pooled and acidified with formic acid to a final concentration of 10%. Finally, samples were dried using a SPEED-VAC™ and pellets were stored at −80° C.

LC-MS/MS Analysis

Dried peptides were reconstituted in 1% TFA containing 20 fmol/μL of a yeast enolase digest. LC-MS/MS was performed as previously described (Casado and Cutillas, Mol Cell Proteomics 10, M110 003079 (January 2011)). Briefly, phosphopeptide pellets were resuspended in 20 μL of 0.1% TFA and 4 mL were loaded in a LC-MS/MS system, which consists of a nanoflow ultra-high pressure liquid chromatography (UPLC, nanoAccuity, Waters) coupled online to an ORBITRAP™-XL mass spectrometer (Thermo Fisher Scientific, Hemel Hempstead, UK). The top 5 more intense multiply charged ions were selected for CID fragmentation in multistage activation mode. The resolution of MS1 was set to 60,000.

Data Processing and Statistical Analysis

Peptide identification was by matching of MS/MS data to the SwissProt database (downloaded March 2011) restricted to human entries (22,000 protein entries) using the Mascot search engine (Perkins et al, Electrophoresis 20, 3551 (December 1999)). Mass tolerances were set to 5 ppm and 600 millimass units for parent and fragment ions, respectively. Allowed variable modifications were phosphorylation on Ser, Thr and Tyr, PyroGlu on N-terminus glutamine, and oxidation of methionine. Phosphopeptides having Mascot expectancy <0.05 (about 2% FDR) were included in a database of sites quantifiable by MS. Pescal software (Casado and Cutillas, Mol Cell Proteomics 10, M110 003079 (January 2011) and Cutillas and Vanhaesebroeck, Mol Cell Proteomics 6, 1560 (September 2007)) was then used to obtain peak heights and areas of extracted ion chromatograms (XICs) of phosphopeptides in this database across all the samples being compared. Pescal aligned retention times using those of peptides derived from enolase previously spiked in samples as reference points along chromatograms. The XIC windows were 7 ppm and 2 minutes.

XIC intensity values were normalized to the sum of all values in a sample and to the mean of phosphopeptide intensities across samples. The significance that the means of log 2 transformed data were different across samples was assessed by Student's t-test followed by Benjamini Hochberg multiple testing correction.

Kinase Substrate Enrichment Analysis

Phosphopeptides having a p-value (by t-test of log 2 transformed data) of less than 0.05 were grouped into substrate sets. The common feature of phosphopeptides in these substrate groups was that these had sites known to be phosphorylated by a specific kinase or that the phosphorylated residue was present in the context of predefined phosphorylation motifs. The information on kinase-substrate relationships was obtained from publically available databases, namely PhosphoSite (Hornbeck et al, Proteomics 4, 1551 (June 2004)) and PhosphoElm (Dinkel et al, Nucleic Acids Res 39, D261 (January 2011)), while the list of motifs was obtained from the literature and from an analysis of our dataset using Motif-X (Schwartz and Gygi, Nat Biotechnol 23, 1391 (November 2005)).

Three approaches were used to infer global differences in abundance of substrate groups across samples. The first one involved counting the number of phosphopeptides in the substrate group whose intensities increased or decreased relative to the control. The enrichment of kinase substrates was then calculated by a parameter we term "delta counts", which was defined as the number of phosphopeptides in a substrate group that significantly increase their intensity relative to control minus those that decrease their intensity. The advantage of this approach is that it does not involve divisions and therefore it is applicable to situations where the number of substrates for a particular substrate group is zero in some to the samples being compared. The significance of enrichment was then calculated by the hypergeometric test followed by Benjamini Hochberg multiple testing correction. The second approach investigated here to assess enrichment of substrate groups involved comparing the means (arithmetic average) of the intensities of all the phosphopeptides in a given substrate group in a sample relative to the control. For this, the intensities of phosphopeptides were first normalized to control and log 2 transformed so that these intensities were all expressed relative to control. In addition to derive a value of fold difference of a given substrate group across control and test samples, we also calculated p-values using paired t-test followed by Benjamini Hochberg multiple testing correction. The third approach involved calculating the ratio of means of the phosphopeptide intensities in the substrate groups relative to the phosphopeptide intensities in the whole dataset (i.e. enrichment=mS/mP, where mS: Log 2 mean intensities substrate group; mP: Log 2 mean intensities whole dataset). The significance of enrichment was the calculated using a Z score=$(mS-mP)*m^{1/2}/\delta$ (where m: size of substrate group; δ: standard deviation mean intensities whole dataset). The z score was converted to a p-value in Microsoft Excel 2007. A script was written in Visual Basic for Applications to automate the application of KSEA algorithms.

Results

Principles of Kinase-Substrate Enrichment Analysis (KSEA)

In order to infer kinase activity from phosphoproteomics data we grouped phosphopeptides identified in large-scale phosphoproteomics into substrate groups; these contain phosphorylation sites known to be substrates of specific kinases or share specific phosphorylation motifs. In order to define substrate groups, we obtained information on kinase-substrate relationships from publically available databases of phosphorylation sites, namely PhosphoSite (Hornbeck et al, *Proteomics* 4, 1551 (June 2004)) and PhosphoElm (Dinkel et al, *Nucleic Acids Res* 39, D261 (January 2011)), whereas phosphorylation motifs were obtained from the literature and from Motif-X (Schwartz and Gygi, *Nat Biotechnol* 23, 1391 (November 2005)). A total of 293 and 298 kinases were represented in PhosphoSite and PhosphoElm databases, respectively. Each substrate group had an average of ~17 substrates and a median of 5 substrates per kinase. The number of motifs analyzed was 109. The extent of enrichment of kinase activities was then calculated by considering the intensities of phosphopeptides showing statistically significant differences across experimental samples. Significance of enrichment of kinase activities was then estimated by the hypergeometric test, while statistical significance of differences in mean phosphopeptide intensities was assessed by paired t-test.

Figure 1:
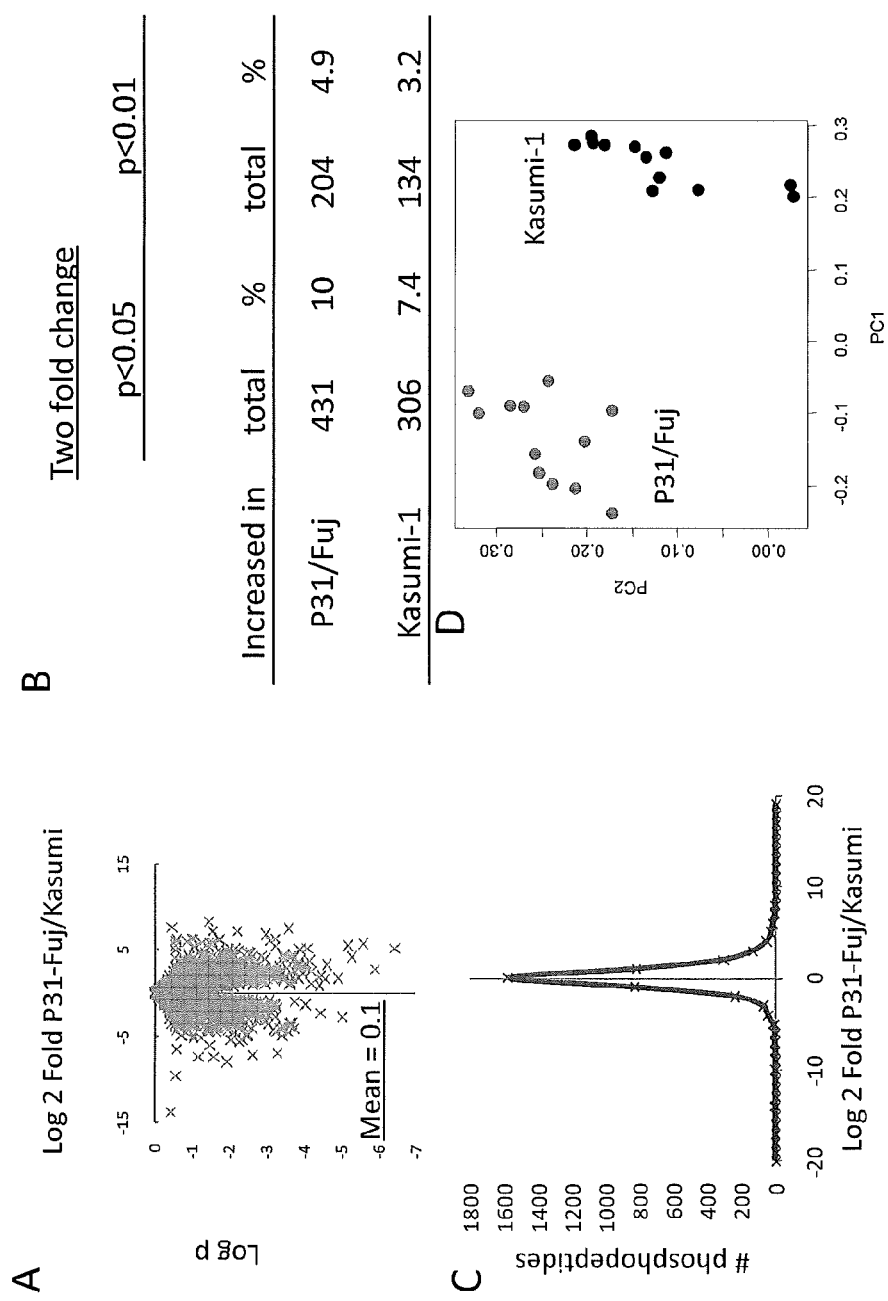
Figure 1:
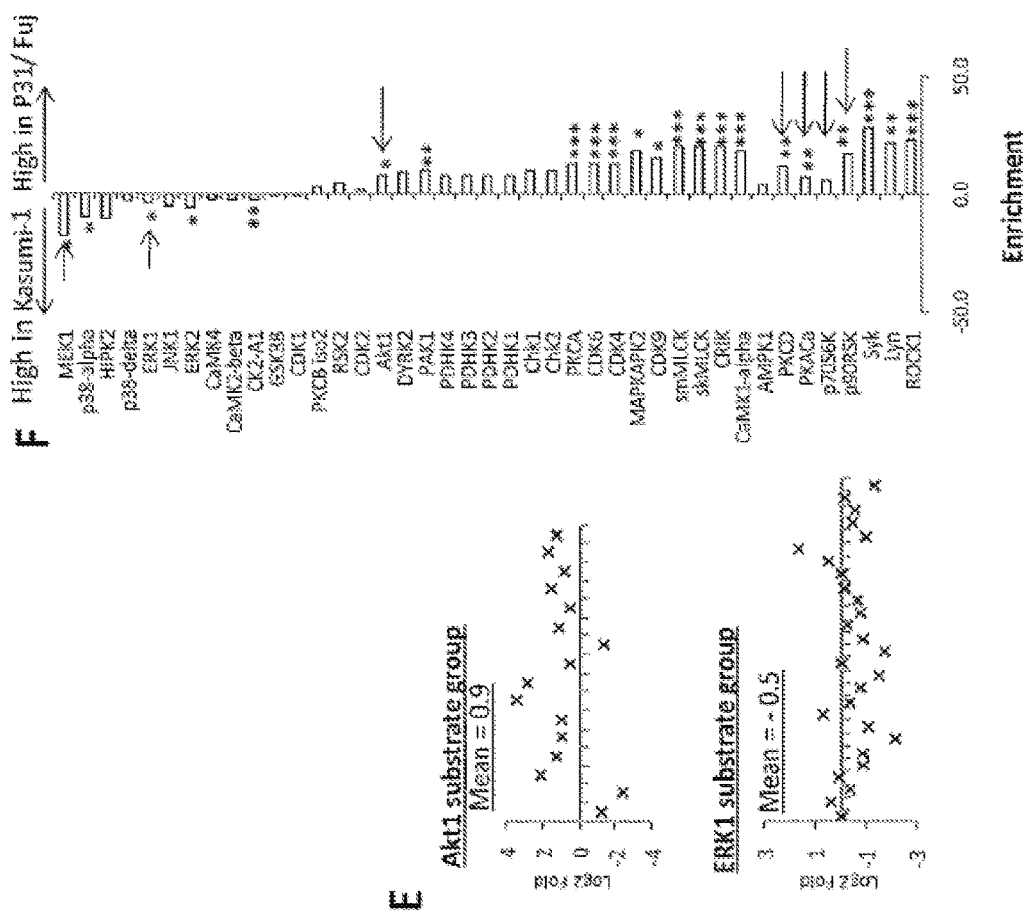

Application of KSEA for Comparison of Phosphoproteomics Data from 2 Different Acute Myeloid Leukemia (AML) Cell Lines KSEA may be better explained by illustrating its use to an experiment in which the phosphoproteomes of two AML cell lines, namely, P31/Fuj and Kasumi-1, were compared. We were interested in comparing these cell lines because of their genetic background in terns of PI3K activation (P31/Fuj and Kasumi-1 are PTEN negative and positive respectively) and their sensitivity to inhibition of proliferation by signaling inhibitors is also very different, with P31/Fuj being multi-drug resistant relative to Kasumi-1 (Casado and Cutillas, *Mol Cell Proteomics* 10, M110 003079 (January 2011). The phosphoproteome of both AML cell lines were analyzed using LC-MS/MS methodology previously described (Casado and Cutillas, *Mol Cell Proteomics* 10, M110 003079 (January 2011). Three biological replicates per cell line were analyzed in each experiment and each experiment was repeated 3 times leading to a total of 9 biological replicates per cell line. A total of 4300 phosphopeptides were quantified across the cell lines, with 431 and 306 of these being preferentially phosphorylated in P31/Fuj or Kasumi-1 cells, respectively with a cut-off p-value <0.05; of these, 204 and 134 phosphopeptides had a p-value <0.01 (FIGS. 1A and B). The intensities of most phosphopeptides were not significantly different between the cell lines (FIG. 1B) and log 2 fold changes centered around zero (no change, FIG. 1C). Nevertheless, the observed differences were sufficient to separate P31/Fuj and Kasumi-1 samples based on principal component analysis (PCA, FIG. 1D).

We then applied KSEA to the phosphoproteomics data by linking quantified phosphorylation sites to kinases using the two different strategies outlined above: i) matching of phosphorylation sites to substrate databases and ii) grouping phosphorylation sites into motifs which can then be assigned to different kinase groups.

Figure 2:
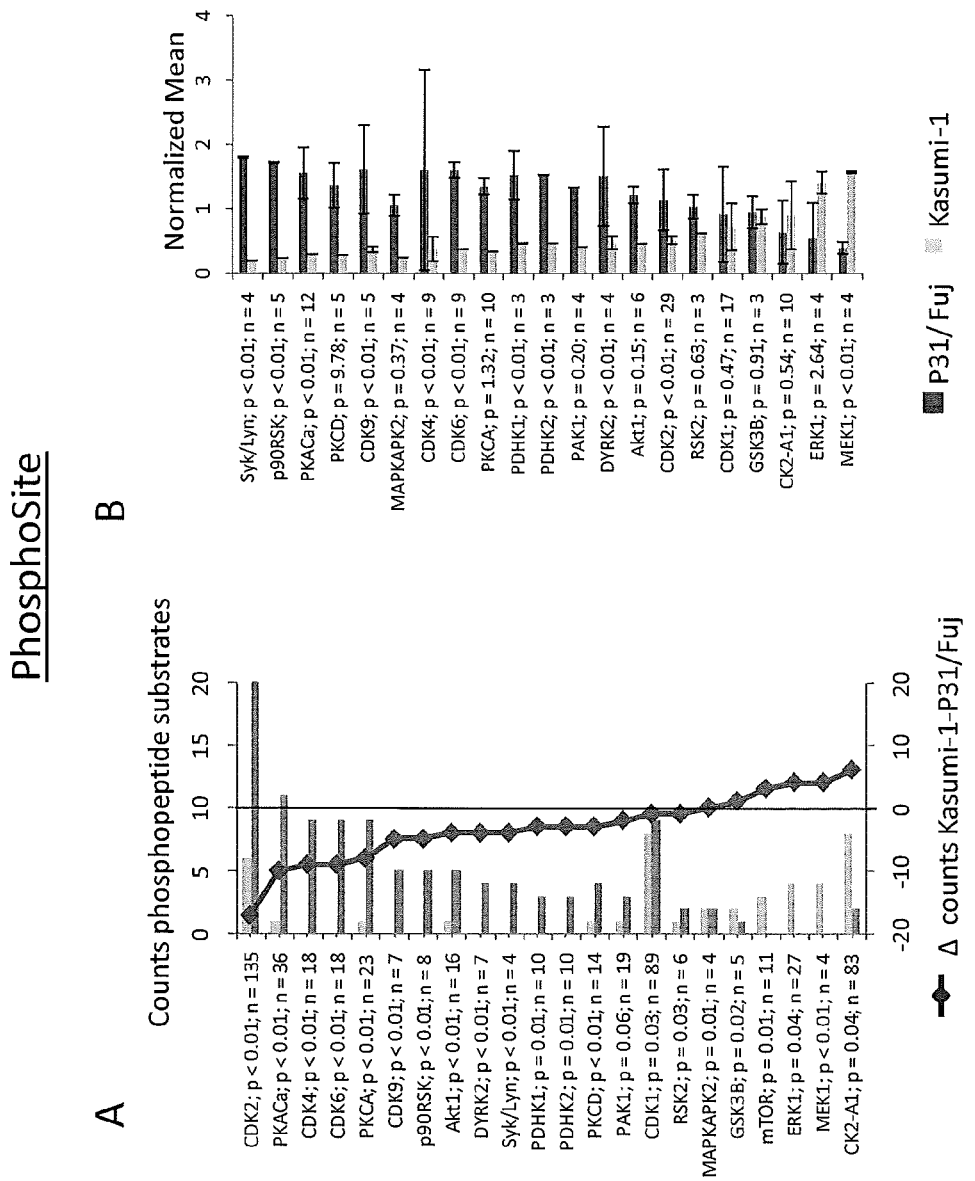

FIG. 2 show the results obtained when two different methods to quantify enrichment were used taking the phosphoSite database as the source of kinase-substrate relationships. As a measure of substrate group enrichment, we counted the substrates significantly increased in Kasumi-1 and subtracted them to those significantly increased in P31/Fuj for each kinase; these values, which we term delta counts, are shown in FIG. 2A for all of the kinases matched to at least three phosphorylation site substrates. The hypergeometric test was then used to assess the significance of enrichment of the phosphorylation sites that are significantly increased or decreased relative to the total number of sites for that particular kinase (FIG. 2A). As an additional test to assess enrichment of substrate groups, we also compared the means of substrate intensities between the two cell lines for each kinase (FIG. 2B).

Significance of differences between means was assessed by paired t-test. Both types of analysis indicated that the phosphorylation of substrates for CDKs, PKA, PKB/AKT, PKC, P90RSK, DYRK2, PAK and ROCK was significantly enriched in P31/Fuj cells (FIG. 2) while substrates for CK2, MEK1 and ERK1 were significantly enriched in Kasumi-1 cells (FIG. 2). The same analysis was performed using the phosphoElm database (FIG. 3) as the source of kinase-substrate relationships. These analyses showed a remarkable agreement in the results regardless of which database or statistical test was used as the basis for KSEA. Substrates of kinases whose phosphorylation was enriched included those for PKC, PKB/AKT, RSK and PAK in P31/Fuj and an enrichment of CK2 and those for MEK and ERK activities in Kasumi-1 cells, suggesting that these kinases were more active in the respective cell line.

Figure 3:
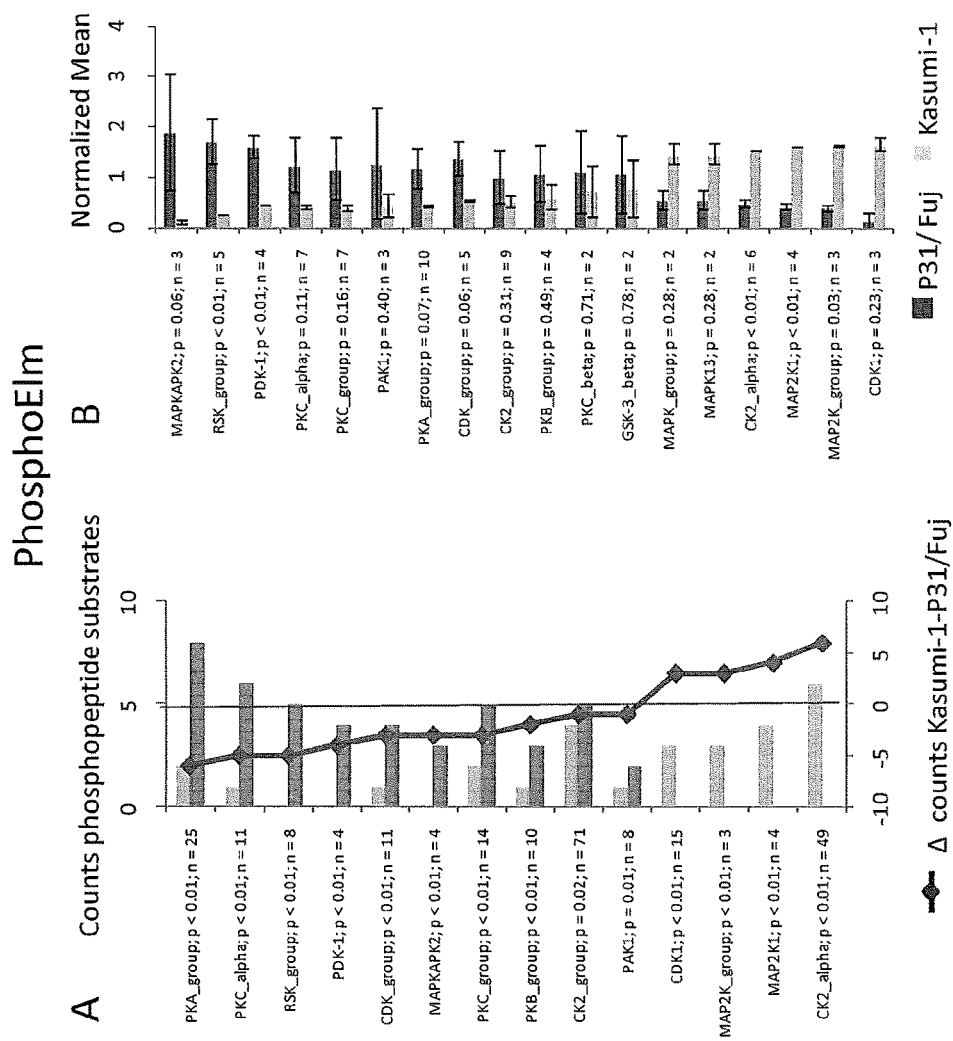
Figure 4:
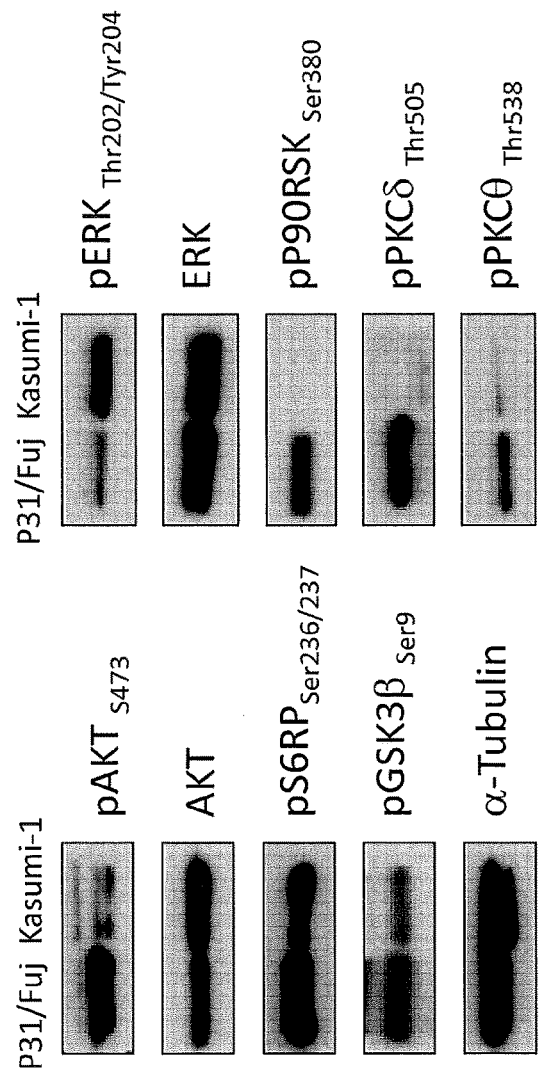
FIG. 4 is a Western blot confirming the results obtained by KSEA and shows the phosphorylation of proteins on sites known to correlate with the activity of kinases shown with an arrow in FIG. 1F.

In order to validate the results of KSEA, Western blot was used to measure phosphorylation sites that correlate with the activity of selected kinases identified to be differentially regulated or on proteins known to be phosphorylated by some of these kinases (FIG. 4). Thus, the phosphorylation of Ser-473 AKT, Ser-380 P90RSK, Thr-505 PKCδ and Thr-538 PKCθ (all of which correlate with their activity state) were increased in P31/Fuj cells relative to Kasumi-1, while the phosphorylation of ERK at Thr202/Tyr204 was more prominent in Kasumi-1 cells (FIG. 4). The phosphorylation of GSK3β at Ser-9 and 6SRP at Ser-236/237 which are catalyzed by AKT and RSK, respectively, were also increased in P31/Fuj (FIG. 4). These results are consistent with, and thus validate, those obtained by KSEA of large scale MS-based phosphorylation data shown in FIGS. 2 and 3.

Figure 5:
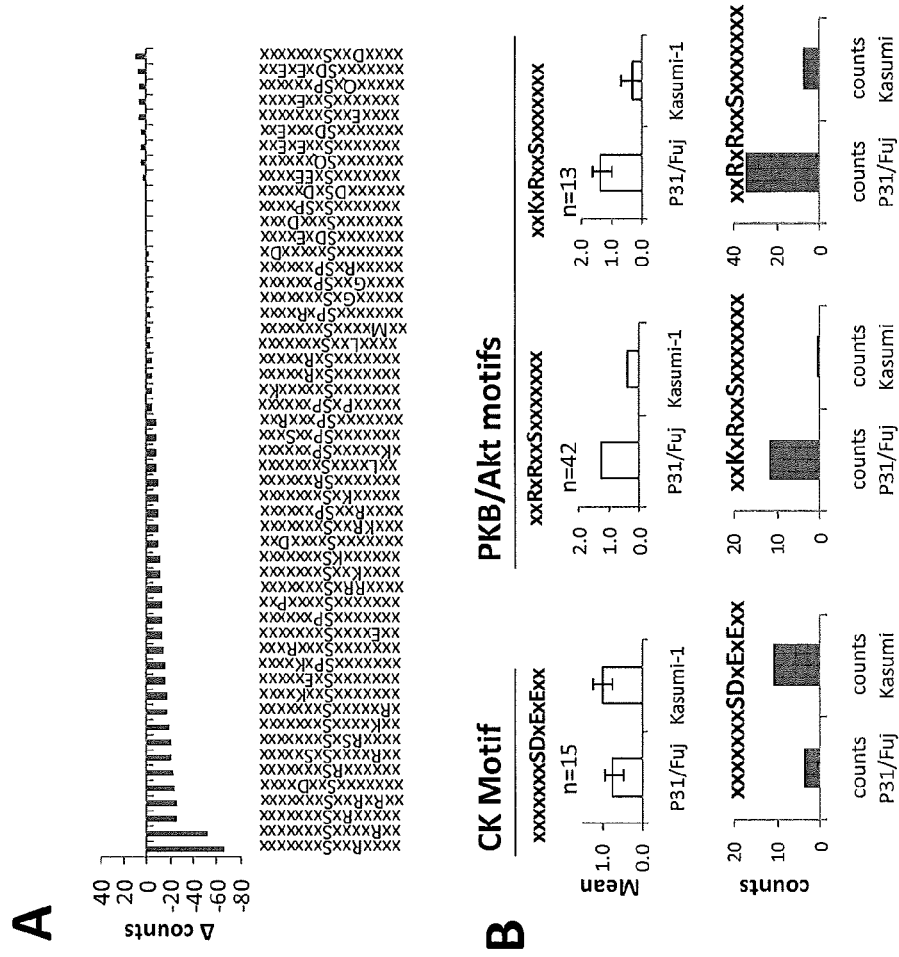
FIGS. 5A and 5B show comparative KSEA of P31/Fuj and Kasumi-1 cell lines based on phosphorylation motifs. (A) Overview of substrate group enrichment based on common phosphorylation motifs. (B) Illustrative examples of substrate groups enriched in either cell line.

The KSEA algorithms were also applied to find phosphorylation motifs differentially phosphorylated in P31/Fuj and Kasumi-1 cells. The analysis based on both delta counts and comparison of means indicated that acidic motifs tended to be more phosphorylated in Kasumi-1 cells, whereas basophilic motifs were more phosphorylated in P31/Fuj cells (FIG. 5A). In both cases the phosphorylation the motifs RxRxxS and KxRxxS, that are associated with PKB/AKT and RSK isoforms, were more phosphorylated in P31/Fuj cells relative to Kasumi-1, whereas the SDxExE motif, associated to CK2, was predominantly more phosphorylated in Kasumi-1 cells (FIG. 5B). These results are thus consistent with those obtained from KSEA based on databases of kinase-substrate relationships (FIGS. 2 and 3).

The present inventor has therefore found that quantifying the enrichment of substrates (previously found to be differentially regulated by large-scale phosphoproteomics) that belong to predefined groups can predict kinase pathway activation with a good degree of accuracy.

EXAMPLE 2—HETEROGENEITY OF SUBSTRATE GROUP PHOSPHORYLATION ACROSS PRIMARY AML

Figure 7:
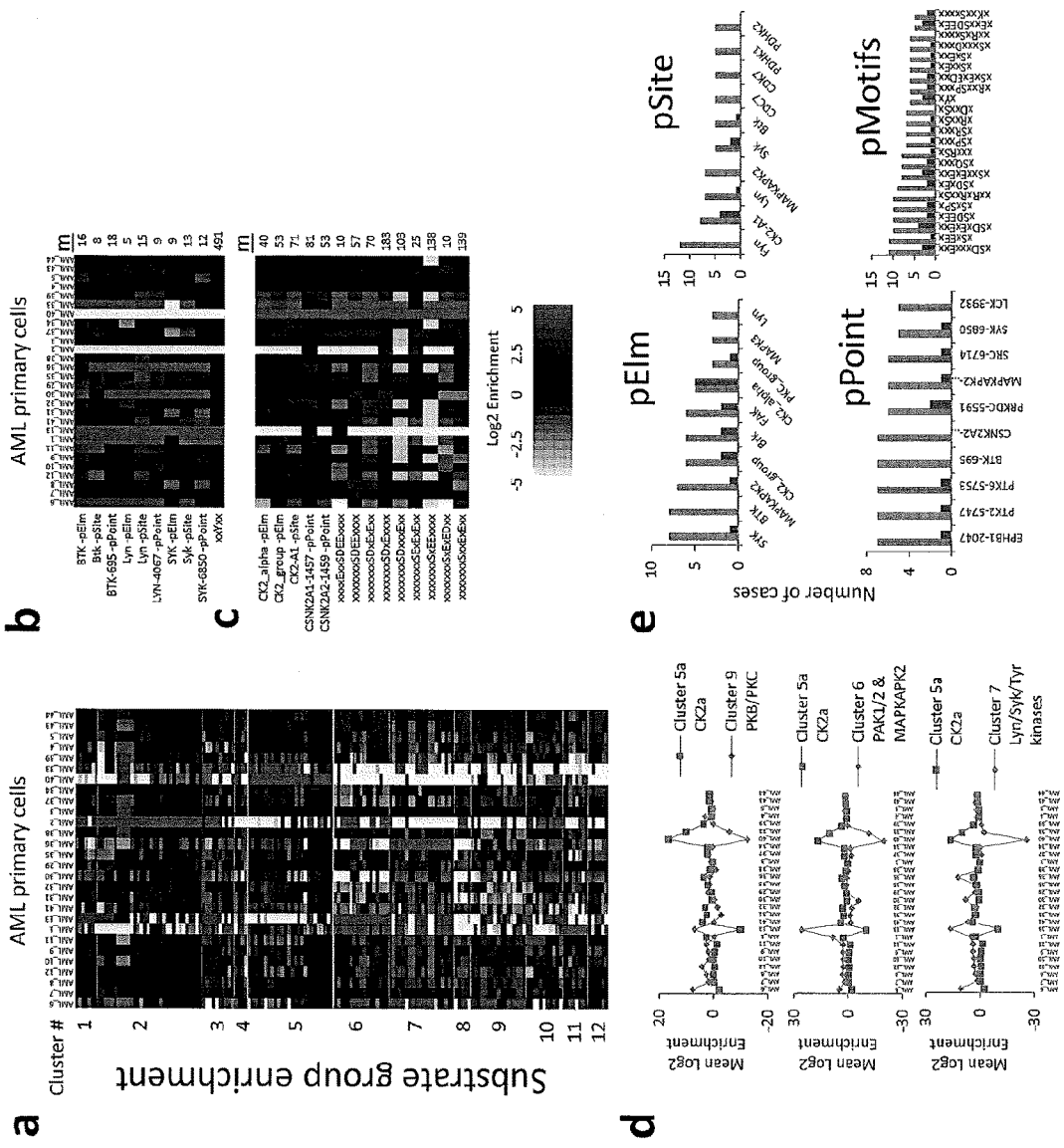

To characterize kinase signaling heterogeneity in primary AML, substrate group enrichment was measured across the 28 AML cases shown in FIG. 7. The enrichment data was pooled based on four different sources of kinase-substrate relationships, namely phosphoElm, phosphoPoint, phosphoSite, and the inventor's collection of phosphorylation motifs. Unsupervised hierarchical clustering of the enrichment data showed twelve main clusters.

The databases phosphoElm, phosphoSite and phosphoPoint use inconsistent nomenclature to name protein kinases, and these list different sets of substrates per kinases (with only partial overlap). Nevertheless, close inspection of the substrate enrichment clusters indicated that the enrichment data was in general consistent across primary AML, irrespective of the source of the substrate groups used for KSEA. For example, the substrate groups named MAPK_group, MAPK3 and ERK1 in phosphoElm, phosphoPoint and phosphoSite, respectively, all of which consist of substrates of Mitogen Activated Protein Kinases, grouped together in Cluster 1. Similarly, Cluster 1 also contained substrates for CDK_group (phosphoElm), CDC2 (phosphoPoint) and CDK1 (phosphoSite), all of which are different names for cyclin-dependent protein kinase 1. These data are consistent with MAPKs and CDKs having a similar spectrum of motif substrates and with their coregulation, and suggest that these two kinase activities are co-expressed in the AML panel tested. It was also interesting to observe that DNA-PK (named as PRKDC, its gene name, in phosphoPoint) and ATM substrate groups clustered with the group defined by the xSQx motif; these substrate groups are shown in Cluster 11. These data are consistent with the known substrate specificity of DNA-PK and ATM. Other representative associations include the enrichment of protein tyrosine kinase substrates in Cluster 7, in which Btk, Syk and Lyn substrates showed similar patterns of enrichment irrespective of the substrate-group database used for the analysis (FIG. 7). The phosphotyrosine motif clustered with these substrate groups, although other tyrosine kinases grouped with other clusters. It was also interesting to observe that Casein Kinase 2α substrates (named as CSNK2A1, CSNK2A2 by phosphoPoint and CK2 by phosphoElm and phosphoSite) grouped in Cluster 5, which also contained several phosphorylation motifs rich in acidic residues at the C-tem. Similarly, the enrichment of most substrate groups defined by basic motifs clustered with those defined by protein kinase A and protein kinase C (Cluster 2). These data are consistent with the known substrate specificities of PKA, PKC and casein kinases and further indicate that CK2α and basophilic kinase activities are differentially expressed across our panel of primary AML.

In addition to positive correlations of substrate groups defined by kinases and motifs, we also observed negative correlations in the expression of certain kinase-substrate groups. For example the substrate groups enriched in cluster 5a comprising acidic motifs and CK2α substrates negatively correlated with those in clusters 9, 6 and 7 comprising PKB/PKC, PAK/MAPAPK2 and Lyn/Syk/Try substrates, respectively (FIG. 7). These results indicate that CK2α kinase activity tends to be mutually exclusive with basophilic and tyrosine kinase activities in primary AML.

FIG. 7e shows that substrate groups more frequently enriched in primary AML include those for the tyrosine kinases Syk, Btk, and Lyn. As for the serine/threonine kinases, casein kinase and MAPKAPK2 substrates were also found to be consistently enriched. The motifs showing more frequent increase included those in acidic sequences (CK2 motifs, 11 cases), the RxRxxS motif (10 cases), the SQ motif (8 cases) and the tyrosine motif (6 cases).

The invention claimed is:

1. A method of identifying an activated protein modifying enzyme in a sample using mass spectrometry, comprising the following steps, carried out in order:
    (a) adding reference modified peptides to peptides obtained from a first sample and a second sample to produce a first mixture of peptides and reference modified peptides and a second mixture of peptides and reference modified peptides, respectively;
    (b) carrying out mass spectrometry on the first mixture to obtain data relating to the peptides from the first sample, and on the second mixture to obtain data relating to the peptides from the second sample;
    (c) comparing the data relating to the peptides from the first and second samples with data in a database of modified peptides to identify modified peptides in the first and second samples;
    (d) grouping the modified peptides from the first and second samples into a single group according to one of the following parameters:
        (1) modified peptides having a modification site that is modified by the same protein modifying enzyme; or
        (2) modified peptides having a modification site that is part of the same modification motif;
    (e) calculating enrichment of the modified peptides from the first sample compared to the modified peptides from the second sample in the group; and
    (f) calculating the statistical significance of said enrichment;
    wherein a statistically significant enrichment is indicative of a protein modifying enzyme being activated in the first sample compared to the second sample.

2. The method according to claim 1, wherein the database of modified peptides is compiled by a method comprising:
    i obtaining peptides from a sample;
    ii enriching modified peptides from the peptides obtained in step i;
    iii carrying out liquid chromatography-tandem mass spectrometry (LC-MS/MS) on the enriched modified peptides obtained in step ii;
    iv comparing the modified peptides detected in step iii to a known reference database in order to identify the modified peptides; and
    v compiling data relating to the modified peptides identified in step iv into a database.

3. The method according to claim 2, wherein (a) step ii is carried out using multidimensional chromatography, optionally wherein the multidimensional chromatography is carried out using either strong cation exchange high performance liquid chromatography (SCX-HPLC), immobilized metal ion affinity chromatography (IMAC) and titanium dioxide ($TiO_2$) chromatography or anion exchange high performance liquid chromatography (SAX-HPLC), immobilized metal ion affinity chromatography (IMAC) and titanium dioxide ($TiO_2$) chromatography; or (b) step ii is carried out using antibody-based methods.

4. The method according to claim 2, wherein step iv is carried out using the MASCOT search engine.

5. The method according to claim 2, wherein the data relating to the modified peptides identified in step iv is selected from the group consisting of identity of the modified peptide, mass to charge (m/z) ratio, charge (z) and relative retention time of the modified peptide.

6. The method according to claim 2, wherein step iv is carried out using the ProteinProspector™ or SEQUEST® search engines.

7. The method according to claim 1, wherein step (a) further comprises enriching modified peptides from said first and second mixtures of peptides and reference modified peptides to produce a first and second mixture of enriched modified peptides respectively, and step (b) comprises carrying out mass spectrometry on said first and second mixtures of enriched modified peptides to obtain data relating to the modified peptides in the first and second samples.

8. The method according to claim 7, wherein the step of enriching modified peptides is carried out using chromatography, optionally wherein the chromatography is selected from the group consisting of immobilized metal ion affinity chromatography (IMAC), titanium dioxide ($TiO_2$) chromatography and zirconium dioxide ($ZrO_2$) chromatography.

9. The method according to claim 7, wherein the step of enriching modified peptides is carried out using antibody-based methods.

10. The method according to claim 1, wherein the data relating to the peptides from the first and second samples comprises the mass to charge (m/z) ratio, charge (z) and relative retention time of the peptides from the first and second samples; and/or wherein said mass spectrometry in step (b) is liquid chromatography-mass spectrometry (LC-MS).

11. The method according to claim 1, wherein the MS technique uses isotope labels for quantification.

12. The method according to claim 11, wherein the MS technique uses metabolic labeling or chemical derivatization.

13. The method according to claim 12, wherein the metabolic labeling comprises using stable isotope labeled amino acids in culture (SILAC) or wherein the chemical derivatization is iTRAQ, ICAT, or TMT.

14. The method according to claim 1, further comprising after step (c) and before step (d):
 (c') calculating the statistical significance of the differential occurrence of the modified peptides between the first and second samples; and
 (c") selecting for use in subsequent steps of the method only modified peptides with a statistically significant differential occurrence between the first and second samples, wherein the modified peptides referred to in steps (d) to (e) are the modified peptides selected in step (c").

15. The method according to claim 1, wherein the protein modifying enzyme is a protein kinase, the reference modified peptides are reference phosphorylated peptides, the modified peptides are phosphorylated peptides, the modification site that is modified by the same protein modifying enzyme is a phosphorylation site that is phosphorylated by the same protein kinase and the modification site that is part of the same modification motif is a phosphorylation site that is part of the same phosphorylation motif.

* * * * *